US010363425B2

(12) United States Patent
Ritter

(10) Patent No.: US 10,363,425 B2
(45) Date of Patent: Jul. 30, 2019

(54) DISCRETE COFIRED FEEDTHROUGH FILTER FOR MEDICAL IMPLANTED DEVICES

(71) Applicant: AVX Corporation, Fountain Inn, SC (US)

(72) Inventor: Andrew P. Ritter, Simpsonville, SC (US)

(73) Assignee: AVX Corporation, Fountain Inn, SC (US)

( * ) Notice: Subject to any disclaimer, the term of this patent is extended or adjusted under 35 U.S.C. 154(b) by 355 days.

(21) Appl. No.: 15/140,751

(22) Filed: Apr. 28, 2016

(65) Prior Publication Data

US 2016/0346555 A1 Dec. 1, 2016

Related U.S. Application Data

(60) Provisional application No. 62/169,201, filed on Jun. 1, 2015.

(51) Int. Cl.
| | |
|---|---|
| *A61N 1/375* | (2006.01) |
| *H01F 27/33* | (2006.01) |
| *H01F 27/40* | (2006.01) |
| *H01G 4/228* | (2006.01) |
| *H01G 4/35* | (2006.01) |
| *H01G 4/38* | (2006.01) |
| *H03H 7/01* | (2006.01) |
| *H01G 2/04* | (2006.01) |

(Continued)

(52) U.S. Cl.
CPC .......... *A61N 1/3754* (2013.01); *H01F 27/33* (2013.01); *H01F 27/40* (2013.01); *H01G 2/04* (2013.01); *H01G 4/228* (2013.01); *H01G 4/242* (2013.01); *H01G 4/35* (2013.01); *H01G 4/38* (2013.01); *H03H 1/0007* (2013.01); *H03H 7/0115* (2013.01); *H03H 2001/0042* (2013.01)

(58) Field of Classification Search
CPC ........ A61N 1/3754; H01F 27/33; H01F 27/40
See application file for complete search history.

(56) References Cited

U.S. PATENT DOCUMENTS

| | | | |
|---|---|---|---|
| 5,782,891 A | 7/1998 | Hassler et al. | |
| 5,973,906 A * | 10/1999 | Stevenson | A61N 1/3754 361/302 |
| 6,008,980 A | 12/1999 | Stevenson et al. | |

(Continued)

FOREIGN PATENT DOCUMENTS

| | | |
|---|---|---|
| WO | WO 02/37511 A1 | 5/2002 |
| WO | WO 2009117599 A2 | 9/2009 |

OTHER PUBLICATIONS

Preliminary Search Report and Written Opinion for FR1654560, 6 pages.

*Primary Examiner* — Scott Bauer
(74) *Attorney, Agent, or Firm* — Dority & Manning, P.A.

(57) ABSTRACT

Discrete cofired feedthrough filters are provided for medical implanted device applications. A plurality of discrete vertical feedthrough filter elements are respectively associated with a plurality of signal wires or pins otherwise supported by an insulating feedthrough and a ferrule. The resulting discrete device comprises a single-element device which is cheaper to make, and which reduces cross-talk between adjacent signal wires/pins while otherwise accommodating changes in feedthrough pitch without having to redesign the filter.

32 Claims, 10 Drawing Sheets

(51) Int. Cl.
*H01G 4/242* (2006.01)
*H03H 1/00* (2006.01)

(56) References Cited

U.S. PATENT DOCUMENTS

| | | | |
|---|---|---|---|
| 6,275,369 B1 | 8/2001 | Stevenson et al. | |
| 6,349,025 B1 | 2/2002 | Fraley et al. | |
| 6,414,835 B1 | 7/2002 | Wolf et al. | |
| 6,473,291 B1 | 10/2002 | Stevenson | |
| 6,490,148 B1 | 12/2002 | Allen et al. | |
| 6,643,903 B2 | 11/2003 | Stevenson et al. | |
| 6,765,779 B2 | 7/2004 | Stevenson et al. | |
| 6,768,629 B1 | 7/2004 | Allen et al. | |
| 6,778,040 B2 * | 8/2004 | Kim | H01R 13/719 333/182 |
| 6,882,248 B2 | 4/2005 | Stevenson et al. | |
| 6,920,673 B2 | 7/2005 | Allen et al. | |
| 6,960,366 B2 | 11/2005 | Ritter et al. | |
| 6,985,347 B2 | 1/2006 | Stevenson et al. | |
| 6,987,660 B2 | 1/2006 | Stevenson et al. | |
| 6,999,818 B2 | 2/2006 | Stevenson et al. | |
| 7,035,076 B1 | 4/2006 | Stevenson | |
| 7,035,077 B2 | 4/2006 | Brendel | |
| 7,128,765 B2 | 10/2006 | Paulot et al. | |
| 7,136,273 B2 | 11/2006 | Stevenson et al. | |
| 7,164,572 B1 | 1/2007 | Burdon et al. | |
| 7,489,495 B2 | 2/2009 | Stevenson | |
| 7,535,693 B2 | 5/2009 | Stevenson et al. | |
| 7,551,963 B2 | 6/2009 | Rusin et al. | |
| 7,564,674 B2 | 7/2009 | Frysz et al. | |
| 7,569,452 B2 | 8/2009 | Fu et al. | |
| 7,623,336 B2 | 11/2009 | Stevenson et al. | |
| 7,765,005 B2 | 7/2010 | Stevenson | |
| 7,797,048 B2 | 9/2010 | Stevenson et al. | |
| 7,804,676 B2 | 9/2010 | Brendel et al. | |
| 7,853,324 B2 | 12/2010 | Stevenson et al. | |
| 7,853,325 B2 | 12/2010 | Dabney et al. | |
| 7,899,551 B2 | 3/2011 | Westlund et al. | |
| 7,917,219 B2 | 3/2011 | Stevenson et al. | |
| 7,945,322 B2 | 5/2011 | Stevenson et al. | |
| 7,957,806 B2 | 6/2011 | Stevenson et al. | |
| 7,966,075 B2 | 6/2011 | Johnson et al. | |
| 8,000,801 B2 | 8/2011 | Stevenson et al. | |
| 8,095,224 B2 | 1/2012 | Truex et al. | |
| 8,116,862 B2 | 2/2012 | Stevenson et al. | |
| 8,145,324 B1 | 3/2012 | Stevenson et al. | |
| 8,155,760 B2 | 4/2012 | Westlund et al. | |
| 8,175,700 B2 | 5/2012 | Johnson et al. | |
| 8,179,658 B2 | 5/2012 | Brendel et al. | |
| 8,180,448 B2 | 5/2012 | Stevenson et al. | |
| 8,200,328 B2 | 6/2012 | Stevenson et al. | |
| 8,224,462 B2 | 7/2012 | Westlund et al. | |
| 8,238,075 B2 | 8/2012 | Bultitude et al. | |
| 8,244,370 B2 | 8/2012 | Halperin et al. | |
| 8,275,466 B2 | 9/2012 | Halperin et al. | |
| 8,301,243 B2 | 10/2012 | Stevenson et al. | |
| 8,311,628 B2 | 11/2012 | Stevenson et al. | |
| 8,364,283 B2 | 1/2013 | Halperin et al. | |
| 8,422,195 B2 | 4/2013 | Stevenson | |
| 8,433,410 B2 | 4/2013 | Stevenson et al. | |
| 8,463,375 B2 | 6/2013 | Stevenson et al. | |
| 8,468,664 B2 | 6/2013 | Brendel et al. | |
| 8,577,453 B1 | 11/2013 | Stevenson et al. | |
| 8,626,310 B2 | 1/2014 | Barror et al. | |
| 8,642,887 B1 | 2/2014 | Li et al. | |
| 8,644,936 B2 | 2/2014 | Iyer et al. | |
| 8,648,255 B2 | 2/2014 | Talamine et al. | |
| 8,648,265 B2 | 2/2014 | Talamine et al. | |
| 8,649,857 B2 | 2/2014 | Stevenson et al. | |
| 8,653,384 B2 | 2/2014 | Tang et al. | |
| 8,659,870 B2 | 2/2014 | Brendel et al. | |
| 8,660,645 B2 | 2/2014 | Stevenson et al. | |
| 8,751,013 B2 | 6/2014 | Johnson et al. | |
| 8,855,768 B1 | 10/2014 | Johnson et al. | |
| 8,868,189 B2 | 10/2014 | Stevenson et al. | |
| 8,897,887 B2 | 11/2014 | Halperin et al. | |
| 8,903,505 B2 | 12/2014 | Stevenson et al. | |
| 8,938,309 B2 | 1/2015 | Marzano et al. | |
| 8,977,355 B2 | 3/2015 | Stevenson et al. | |
| 9,008,799 B2 | 4/2015 | Stevenson et al. | |
| 9,014,808 B2 | 4/2015 | Stevenson et al. | |
| 9,042,999 B2 | 5/2015 | Stevenson et al. | |
| 9,061,139 B2 | 6/2015 | Stevenson et al. | |
| 9,061,161 B2 | 6/2015 | Iyer et al. | |
| 9,064,640 B2 | 6/2015 | Brendel et al. | |
| 9,065,224 B2 | 6/2015 | Marzano et al. | |
| 9,108,066 B2 | 8/2015 | Woods et al. | |
| 9,119,968 B2 | 9/2015 | Halperin et al. | |
| 9,233,253 B2 | 1/2016 | Stevenson et al. | |
| 9,248,283 B2 | 2/2016 | Halperin et al. | |
| 9,251,960 B2 | 2/2016 | Brendel et al. | |
| 9,352,150 B2 | 5/2016 | Stevenson et al. | |
| 9,427,596 B2 | 8/2016 | Woods et al. | |
| 9,463,329 B2 | 10/2016 | Frysz et al. | |
| 9,492,659 B2 | 11/2016 | Tang et al. | |
| 9,511,220 B2 | 12/2016 | Marzano et al. | |
| 9,575,558 B2 | 2/2017 | Almen et al. | |
| 9,692,173 B2 | 6/2017 | Marzano et al. | |
| 9,764,129 B2 | 9/2017 | Stevenson et al. | |
| 9,889,306 B2 | 2/2018 | Stevenson et al. | |
| 9,895,534 B2 | 2/2018 | Stevenson et al. | |
| 9,931,514 B2 | 4/2018 | Frysz et al. | |
| 9,993,650 B2 | 6/2018 | Seitz et al. | |
| 10,016,595 B2 | 7/2018 | Stevenson et al. | |
| 10,016,596 B2 | 7/2018 | Stevenson et al. | |
| 10,046,166 B2 | 8/2018 | Stevenson et al. | |
| 10,080,889 B2 | 9/2018 | Marzano et al. | |
| 10,099,051 B2 | 10/2018 | Stevenson et al. | |
| 2008/0065181 A1 * | 3/2008 | Stevenson | A61N 1/056 607/115 |
| 2011/0048770 A1 | 3/2011 | Reiterer et al. | |
| 2012/0158078 A1 * | 6/2012 | Moulder | A61N 1/3718 607/9 |
| 2012/0307416 A1 | 12/2012 | Iyer | |
| 2013/0058003 A1 | 3/2013 | Iyer et al. | |
| 2013/0230424 A1 | 9/2013 | Reiterer et al. | |
| 2014/0062618 A1 | 3/2014 | Ritter et al. | |
| 2014/0163646 A1 | 6/2014 | Tischendorf et al. | |
| 2015/0066124 A1 | 3/2015 | Stevenson et al. | |
| 2015/0217111 A1 * | 8/2015 | Stevenson | A61N 1/08 607/63 |

\* cited by examiner

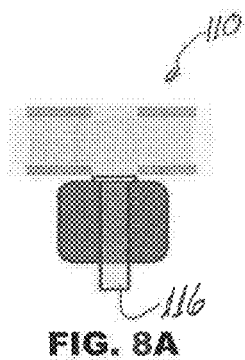
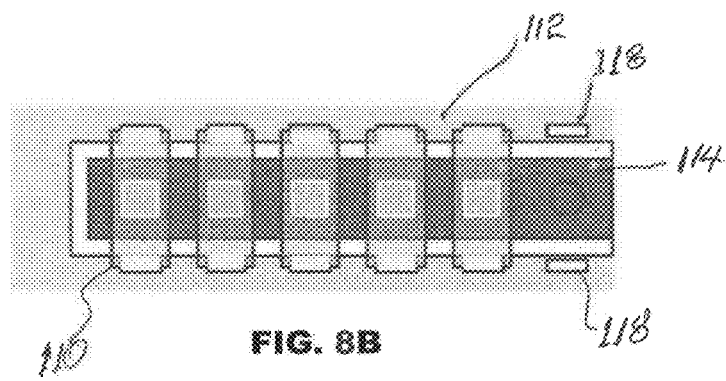
FIG. 8A    FIG. 8B
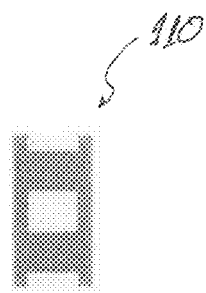
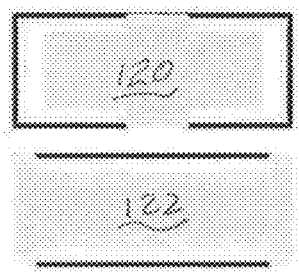
FIG. 8C    FIG. 8D
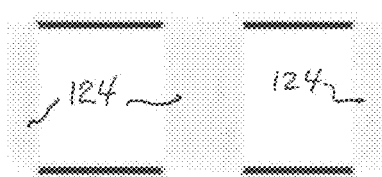
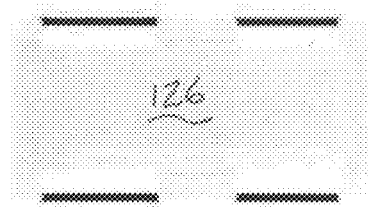
FIG. 8E    FIG. 8F

DISCRETE COFIRED FEEDTHROUGH FILTER FOR MEDICAL IMPLANTED DEVICES

PRIORITY CLAIM

This application claims the benefit of previously filed U.S. Provisional Patent Application entitled "DISCRETE COFIRED FEEDTHROUGH FILTER FOR MEDICAL IMPLANTED DEVICES," assigned U.S. Ser. No. 62/169,201, filed Jun. 1, 2015, and which is incorporated herein by reference for all purposes.

FIELD OF THE SUBJECT MATTER

The presently disclosed technology relates to feedthrough filters and corresponding methodologies. More particularly, the presently disclosed technology relates to manufacturing and use of discrete cofired feedthrough filters for use with active implantable medical devices (AIMD).

BACKGROUND OF THE SUBJECT MATTER

Heart pacemakers and other implantable medical devices include electronic components contained within an outer housing. The outer housing of the implantable medical device can be formed of an appropriate material to withstand implantation within a human body. Implantable electronics can be shielded from external sources of electromagnetic interference (EMI) using a filter.

Conventionally, a feedthrough filter can be coupled to an implantable medical device such that feed wires of the device pass through the feedthrough filter as close as practical to the to the input-output connector on the implanted device. For example, as illustrated in FIGS. 38 and 39 of commonly owned United States Patent Application Publication No. 20140062618, a conventional implantable system 10 can include a canister or ferrule 11 through which feed wires 12 pass in order to connect between external circuitry of an implanted device and internal circuitry of the implanted device. The canister 11 can include a bushing 13 to secure and protect the feed wires 12. Bonding material 14 can be used to secure the feed wires 12 in the canister 11.

Further per such Publication No. 20140062618, a feedthrough filter 15 can be disposed within the canister 11. Feed wires 12 completely pass through feedthrough filter 15 to connect between the internal and external circuitry of the implanted device. The feedthrough filter 15 can act as a capacitor such that the each of the feed wires 12 of the device is electrically connected to a respective set of electrode plates 16 and 17 within the feedthrough filter by the electrically conductive via 18. Conductive plates 17 are interleaved between conductive plates 16 to produce the capacitance effect. However, such feedthrough filters often require numerous intricate manufacturing steps and are susceptible to damage during manufacture and assembly prior to implantation. The complete disclosure of such Publication No. 20140062618 is fully incorporated herein by reference and for all purposes.

Thus, a need exists for an improved electromagnetic interference filter for implantable medical devices. More particularly, it would be desirable to have a filter that can reduce manufacturing cost while also improving installed characteristics. While various implementations of electromagnetic interference filters for implantable medical devices have been developed, no design has emerged that generally encompasses all of the desired characteristics as hereafter presented in accordance with the subject technology.

SUMMARY OF THE SUBJECT MATTER

The presently disclosed subject matter recognizes and addresses various of the foregoing issues, and others concerning certain aspects of filtering devices. Thus, broadly speaking, an object of certain embodiments of the presently disclosed technology is to provide improved designs for certain components and component assemblies associated with filtering devices, and more particularly to provide improved electromagnetic interference filters for implantable medical devices. Other objects, broadly speaking relate to providing discrete cofired feedthrough filters for implanted medical devices and related methodologies.

Aspects and advantages of the presently disclosed subject matter will be set forth in part in the following description, or may be apparent from the description, or may be learned through practice of the presently disclosed subject matter, which relates in some presently disclosed embodiments to an improved electromagnetic interference filter for various electronic devices such as implantable medical devices.

Other present objects relate to construction and surface mounting of discrete filter devices on substrates such as directly on insulated feedthrough arrangements or on other supporting substrates such as printed circuit boards (PCB's) so as to provide both mechanical and electrical connection.

Aspects of other exemplary embodiments of the presently disclosed subject matter provide improved electrical and mechanical coupling of certain mounted devices to circuits or traces on a printed circuit board on which an associated device may be mounted.

Still further aspects of yet still other embodiments of the presently disclosed subject matter provide enhancements to manufacturing and/or mounting methodologies associated with the use of discrete, direct mount type devices.

One exemplary embodiment of presently disclosed subject matter relates to a feedthrough filter arrangement for use with an active implantable medical device (AIMD), comprising a ferrule; a feedthrough associated with such ferrule; a plurality of conductors supported through such feedthrough; and a corresponding plurality of discrete filters. Preferably, each of such filters has at least two respective terminals, with one of such terminals associated with a respective one of such conductors, and the other of such terminals associated with such ferrule.

In some instances thereof, such conductors may comprise respective wire conductors for each of such discrete filters. In others, such ferrule may comprise a metal ferrule; and such feedthrough may comprise an insulating cofired feedthrough which is mounted relative to such metal ferrule.

In another exemplary variation of the foregoing exemplary feedthrough filter arrangement, each of such filters may have side and end terminals, and may have two sets of interleaved vertical electrodes comprising ground electrodes and signal electrodes; each of such ground electrodes may have respective projecting end portions connecting with respective end terminals of each of such filters; and each of such signal electrodes may have respective projecting side portions connecting with respective side terminals of each of such filters.

In another variation thereof, such at least two respective terminals may comprise side and end terminals associated respectively with such filters and such ferrule; and each of such filters may have two sets of interleaved vertical electrodes comprising ground electrodes and signal electrodes.

Per such variation, preferably such ground electrodes are associated with at least one end terminal of each respective filter so that ground is connected to such ferrule, and such signal electrodes are associated with at least one side terminal of each respective filter so that signals on a respective associated conductor are connected to such associated conductor. In some variations thereof, such respective side and end terminals may comprise asymmetrical terminals. For some of those, such feedthrough may include a double row of conductors supported therethrough, and such filters may be mounted on such feedthrough in a row with end terminals thereof on alternate sides of such feedthrough.

In another alternative of such exemplary foregoing feedthrough filter arrangement, side terminals of such filters may comprise respective top and bottom side terminals, with each bottom side terminal respectively connected to the associated conductor of its filter, and with each top side terminal connected to an associated AIMD.

In other alternatives thereof, such respective side and end terminals may include at least a pair of end terminals for each respective filter, and may comprise symmetrical terminals for each respective filter. Per some of such exemplary alternatives, such ferrule may comprise a titanium ferrule with sets of upper surface gold pads attached to ground of such ferrule; and such filters may be mounted relative to such ferrule such that such end terminals for each respective filter are attached to a set of such gold pads of such ferrule. Per others thereof, such conductors may be supported in a single row in such feedthrough, and respective end terminals of each of such filters may be mounted on opposite sides of such feedthrough, with a bottom side terminal of each of such elements situated over respective of such conductors.

For other presently disclosed variations, at least some of such filters may further include additional ground electrodes for relatively lower dcR filter characteristics. Still further, at least some of such filters may further include additional signal electrodes for relatively lower ESR filter characteristics. In some such variations, at least some of such filters further include additional ground electrodes for relatively lower dcR filter characteristics; and additional signal electrodes for relatively lower ESR filter characteristics; and some of such electrodes may comprise relatively lower resistance metals.

In some presently disclosed alternatives, such filters may include relatively low dielectric materials made from NPO dielectric materials. For others, such filters may further include a plurality of dummy electrode layers providing nucleation areas for plating formation of filter terminals. In some such variations, such ground and signal electrodes and such dummy electrode layers may include additional shielding members for relatively increasing the dielectric withstanding voltage characteristics of such filters.

Another exemplary embodiment of presently disclosed subject matter relates to a feedthrough filter arrangement for use in association with external circuitry. Such arrangement preferably comprises a metal ferrule; an insulating feedthrough associated with such ferrule; a plurality of wire conductors supported through such feedthrough; and a corresponding plurality of discrete cofired filter capacitors. Each of such filter capacitors preferably have respective end terminals; a top side terminal; a bottom side terminal; a body of dielectric material; and two sets of interleaved vertical electrodes comprising ground electrodes and signal electrodes received in such body of dielectric material. Further, each of such ground electrodes preferably has respective projecting end portions connecting with respective end terminals of each of such filter capacitors, and each of such signal electrodes preferably has respective projecting side portions connecting with respective side terminals of each of such filter capacitors. Also, respective end terminals of each of such filter capacitors are preferably mounted on opposite sides of such ferrule for a ground connection therewith, and with a bottom side terminal of each of such filter capacitors connected with a respective one of such conductors for a signal connection therewith, so that each of such top side terminals of such filter capacitors are exposed for respective connections with associated external circuitry.

For some such exemplary feedthrough filter arrangements, at least some of such filter capacitors may further include additional ground electrodes for relatively lower dcR filter capacitor characteristics; and additional signal electrodes for relatively lower ESR filter capacitor characteristics. In still other variations thereof, such ferrule may comprise a titanium ferrule with sets of upper surface gold pads attached to ground of such ferrule; and such filter capacitors may be mounted relative to such ferrule such that such end terminals for each respective filter are attached to a set of such gold pads of such ferrule. For some, at least some of such filter capacitors may further include a plurality of dummy electrode layers providing nucleation areas for plating formation of filter capacitor terminals. For other presently disclosed variations, such ground and signal electrodes and such dummy electrode layers may include additional shielding members for relatively increasing the dielectric withstanding voltage characteristics of such filter capacitors.

Still further, it is to be understood that the presently disclosed technology equally applies to the resulting devices and structures disclosed and/or discussed herewith, as well as the corresponding involved methodologies.

One presently disclosed exemplary methodology for a feedthrough filter arrangement for use with an active implanted medical device (AIMD) may preferably comprise providing a metal ferrule; fitting an insulating feedthrough with such ferrule; supporting a plurality of conductors through such feedthrough; and connecting respectively a corresponding plurality of discrete cofired filters with such plurality of conductors, so as to reduce cross-talk between signals on adjacent of such conductors.

Some variations of such presently disclosed methodology may further include providing a double row of conductors supported through such feedthrough; and providing each of such filters with at least one end terminal and at least one side terminal; and mounting such filters on such feedthrough in a row with end terminals thereof on alternate sides of such feedthrough. Other alternatives may further include connecting and directly mounting such plurality of discrete cofired filters with a printed circuit board instead of connecting with such plurality of ferrule conductors.

Yet other variations may further include providing each of such filters with at least two respective terminals, with one of such terminals associated with a respective one of such conductors, and the other of such terminals associated with such ferrule. In some such variations, methodology may further include providing such filter terminals as either symmetrical or asymmetrical terminals.

In still other variations of presently disclosed methodology, such at least two respective terminals may comprise side and end terminals associated respectively with such filters and such ferrule; and each of such filters may have two sets of interleaved vertical electrodes comprising ground electrodes and signal electrodes, so that such ground electrodes are associated with at least one end terminal of each respective filter so that ground is connected to such ferrule, and so that such signal electrodes are associated with at least one side terminal of each respective filter so that signals on a respective associated conductor are connected to such associated conductor. In other alternatives, side terminals of such filters may comprise respective top and bottom side terminals, with each bottom side terminal respectively connected to the associated conductor of its filter, and with each top side terminal connected to an associated AIMD.

Per other variations, each of such filters may comprise filter capacitors having respective end terminals, a top side terminal, a bottom side terminal, a body of dielectric material; and two sets of interleaved vertical electrodes comprising ground electrodes and signal electrodes received in such body of dielectric material. In such instances, preferably each of such ground electrodes have respective projecting end portions connecting with respective end terminals of each of such filter capacitors, and each of such signal electrodes have respective projecting side portions connecting with respective side terminals of each of such filter capacitors.

In other presently disclosed alternatives, methodology may further include selectively providing additional electrodes to such filter capacitors for relatively lower dcR and/or relatively lower ESR filter characteristics. Still other variations may further include selectively providing a plurality of dummy electrode layers to such filter capacitors for providing nucleation areas for plating formation of filter capacitor terminals. Other variations may further include selectively providing additional shielding members to selected of such ground and signal electrodes and such dummy electrode layers for relatively increasing the dielectric withstanding voltage characteristics of such filter capacitors.

For yet other presently disclosed alternatives, respective end terminals of each of such filter capacitors may be mounted on opposite sides of such ferrule for a ground connection therewith, and with a bottom side terminal of each of such filter capacitors connected with a respective one of such conductors for a signal connection therewith, so that each of such top side terminals of such filter capacitors are exposed for respective connections with associated external circuitry.

For others, mounting of such end terminals of such filter capacitors on such ferrule may include using surface tension of solder for self-alignment of such capacitors during a solder reflow step, which causes auto-rotation and centering of the capacitor whenever the solder is heated up for reflow. For some of such variations, presently disclosed methodology may further include attaching a lead to such capacitor after such reflow step, to secure the positioning of such capacitor relative to such ferrule.

Yet further aspects of still other embodiments of the presently disclosed subject matter provide features for improved low series resistance, or improved high breakdown voltage characteristics, or improved lower costs for assembly, or for satisfying needs for specialty configurations.

Additional aspects of the presently disclosed subject matter relate to improvements in single element 3- or 4-terminal feedthrough filters for medical implantable devices. As a single element device, the presently disclosed subject matter is less expensive to manufacture than conventional filters which are constructed as arrays of elements in a single device, with holes for signal wires. Also, the presently disclosed subject matter is advantageous to help reduce cross-talk between adjacent or nearby wires, and can accommodate changes in feedthrough pitch without having to redesign the filter.

Other presently disclosed aspects of improved discrete cofired filter devices are achieved through various combinations of vertically oriented electrodes, paired electrodes, shielded electrodes, and asymmetric terminals. Other presently disclosed aspects of improved discrete cofired filter devices are achieved through various combinations with FCT (fine copper termination) technology. See, for example, commonly owned U.S. Pat. No. 6,960,366 and its related patents, the disclosures of all of which are fully incorporated herein by reference and for all purposes.

Still other aspects of presently disclosed technology are resulting ESL (equivalent series inductance) similar as a conventional FT (feedthrough) array, while having low ESR and dcR in an easily mounted discrete device. Manufacturing costs are low, and shielded structure embodiments have substantially higher working voltage than corresponding non-shielded parts.

Still further, per certain aspects of presently disclosed technology, elimination of top wrap from ground terminal reduces tendency for surface arcing.

Yet further, while the presently disclosed technology is intended for operation in conjunction with an implanted medical feedthrough, it will proved other uses for feedthroughs such as when an associated signal is routed from top to bottom surfaces. For instance, decoupling of high power transistors is one such additional use.

Other presently disclosed embodiments relate to advantageous increases of dielectric withstand voltage (DWV) characteristics through the use of certain presently disclosed shielding features.

It is a further general object to provide relatively low manufacturing costs combined with relatively improved characteristics for discrete cofired feedthrough filter devices.

Additional objects and advantages of the presently disclosed subject matter are set forth in, or will be apparent to those of ordinary skill in the art from, the detailed description herein. Also, it should be further appreciated by those of ordinary skill in the art that modifications and variations to the specifically illustrated, referenced, and discussed features and/or steps hereof may be practiced in various embodiments and uses of the disclosed technology without departing from the spirit and scope thereof, by virtue of present reference thereto. Such variations may include, but are not limited to, substitution of equivalent means, steps, features, or materials for those shown, referenced, or discussed, and the functional, operational, or positional reversal of various parts, features, steps, or the like.

Still further, it is to be understood that different embodiments, as well as different presently preferred embodiments, of this technology may include various combinations or configurations of presently disclosed steps, features or elements, or their equivalents (including combinations of features, configurations, or steps thereof not expressly shown in the figures or stated in the detailed description).

BRIEF DESCRIPTION OF THE DRAWINGS

A full and enabling description of the presently disclosed subject matter, including the best mode thereof, directed to one of ordinary skill in the art, is set forth in the specification, which makes reference to the appended figures, in which:

FIGS. 8A and 8B illustrate, respectively, end and top views (in partial see-through illustration) of a discrete vertical feedthrough filter of presently disclosed subject matter in combination with a supporting ferrule, insulating feedthrough, and terminal wire, similar to the perspective view combination of subject FIG. 6B;

FIG. 8C illustrates an enlarged top view in isolation of the presently disclosed discrete vertical FT filter show in combination illustrated with subject FIGS. 8A and 8B;

Figures 9A, 9B, 9C:
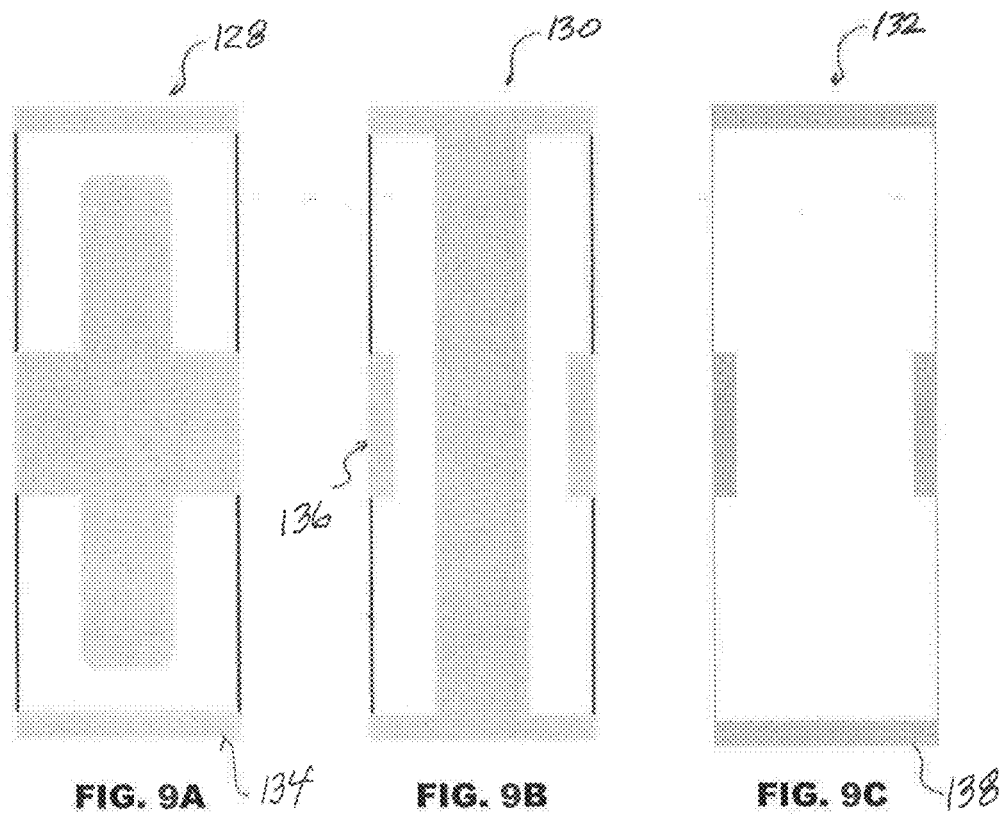
Figures 10A, 10B, 10C:
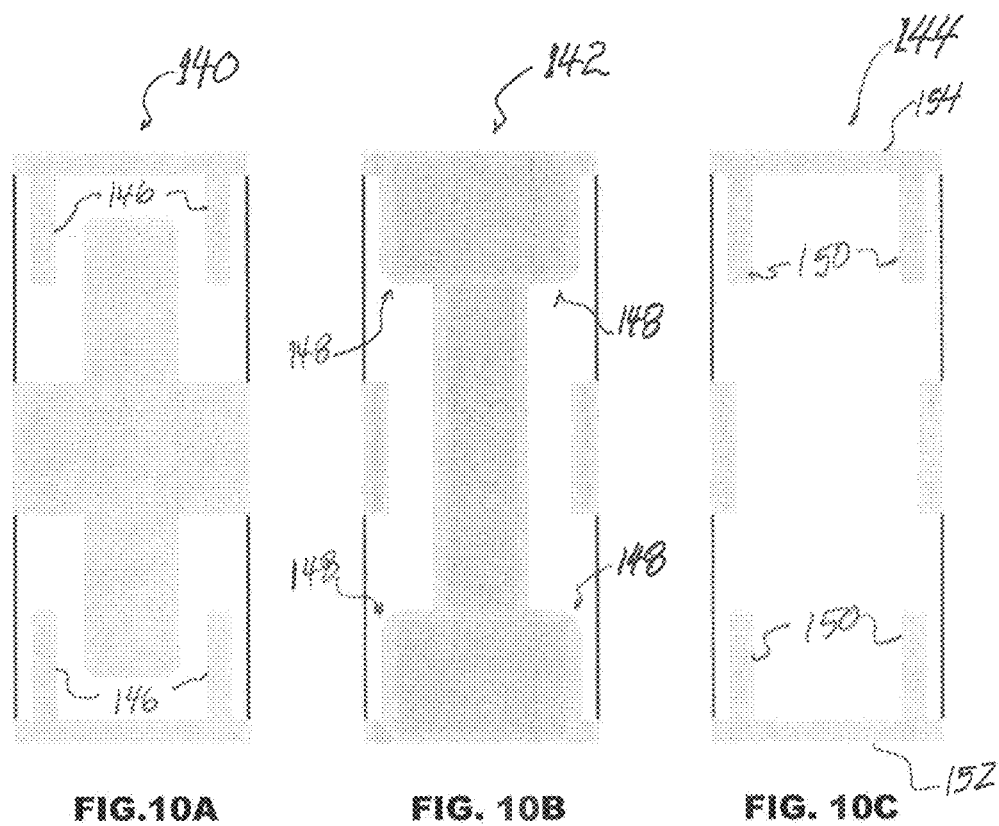
Figure 11A:
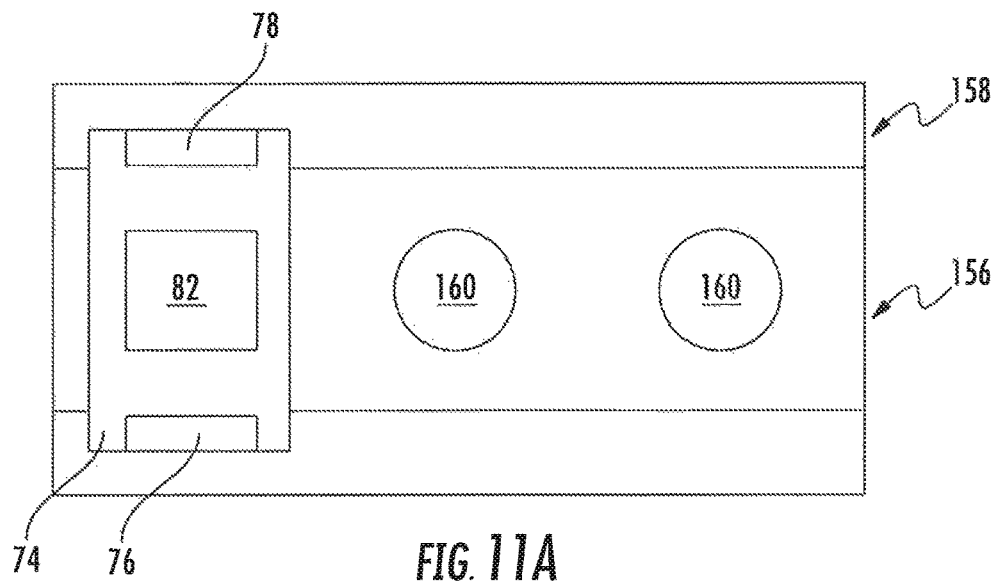
Figure 11B:
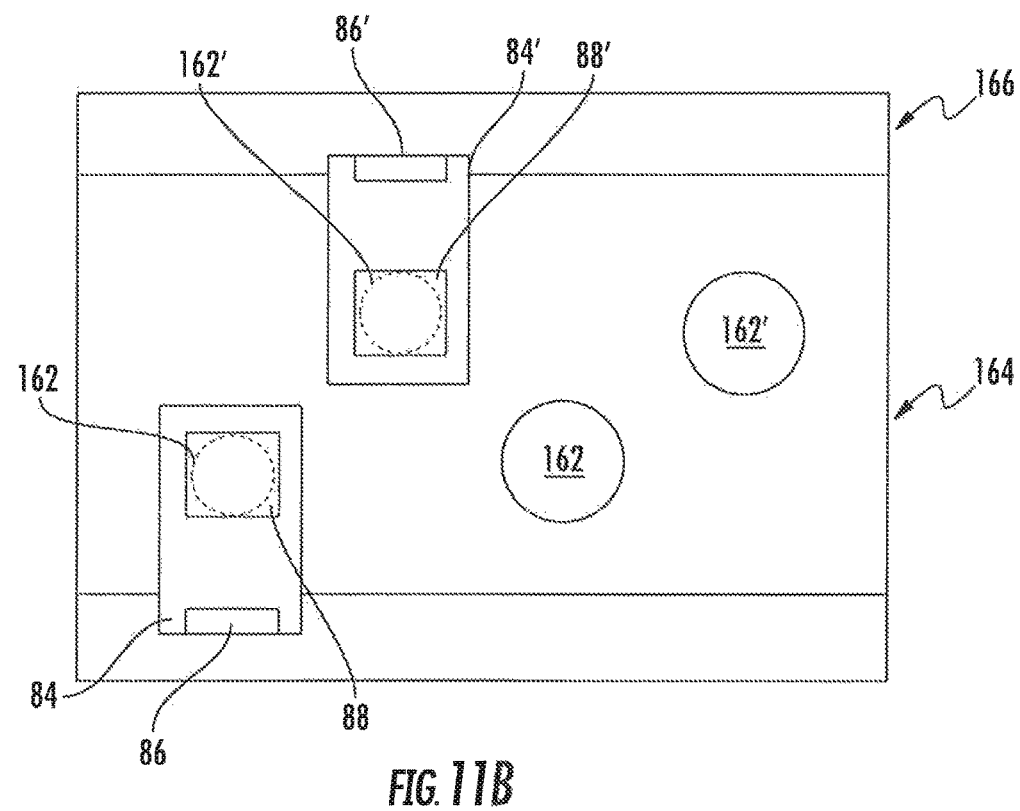

The two respective illustrations of subject FIG. 8D show top views of representative A and B patterns for signal pins of the illustrated exemplary embodiment of present FIG. 8A;

The illustration of subject FIG. 8E shows a top view of a representative pattern for RF pins as may be associated with the illustrated exemplary embodiment of present FIG. 8A;

The illustration of subject FIG. 8F shows a top view of a representative pattern for ground pins as may be associated with the illustrated exemplary embodiment of present FIG. 8A;

The representative preliminary electrode layer designs represented by present FIGS. 9A, 9B, and 9C, illustrate respectively top views of signal, ground, and dummy electrode layers of such design;

Respective FIGS. 10A, 10B, and 10C respectively illustrate signal, ground, and dummy electrode layers as presently disclosed for a shielded design for increasing DWV (dielectric withstand voltage); and FIGS. 11A and 11B represent exemplary alternative device configurations, with FIG. 11A representing a top view of a double-ended filter in association with a single row feedthrough, and FIG. 11B representing a top view of a single-ended filter in association with a double row feedthrough.

Repeat use of reference characters throughout the present specification and appended drawings is intended to represent same or analogous features, elements, or steps of the presently disclosed subject matter.

DETAILED DESCRIPTION OF THE PREFERRED EMBODIMENTS

As discussed in the Summary of the Subject Matter section, the presently disclosed subject matter is generally concerned with improved feedthrough filter devices and related technology and manufacturing and/or mounting methodology thereof. More particularly, the presently disclosed subject matter is concerned with improved designs for certain discrete vertical feedthrough filters and related methodologies.

Selected combinations of aspects of the disclosed technology correspond to a plurality of different embodiments of the presently disclosed subject matter. It should be noted that each of the exemplary embodiments presented and discussed herein should not insinuate limitations of the presently disclosed subject matter. Features or steps illustrated or described as part of one embodiment may be used in combination with aspects of another embodiment to yield yet further embodiments. In additional, certain features may be interchanged with similar devices or features not expressly mentioned which perform the same or similar function.

Figure 1A:
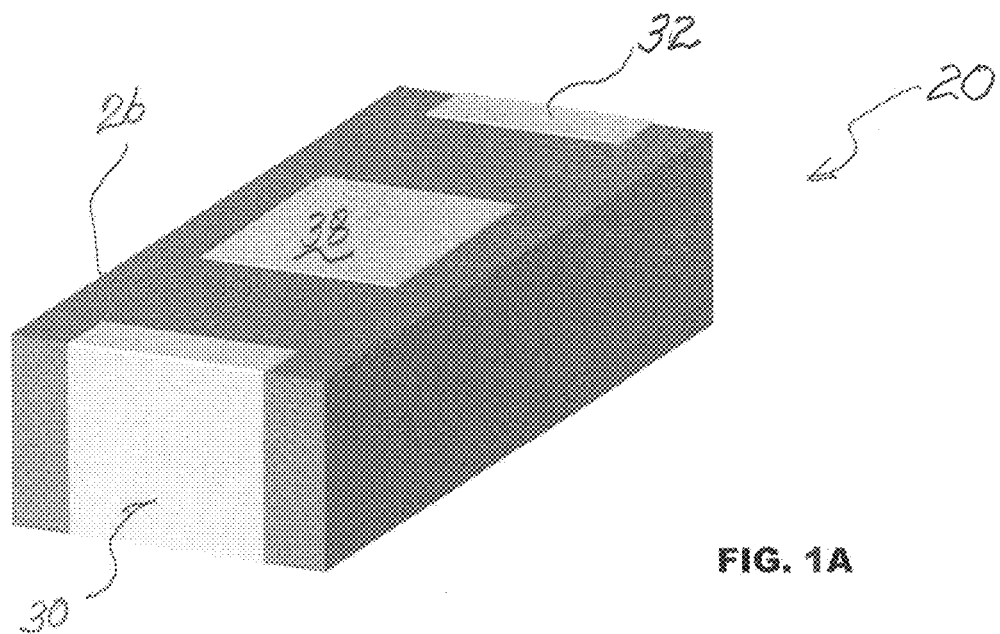
FIG. 1A illustrates a generally sides and top perspective view of an exemplary embodiment in accordance with the presently disclosed technology.

Reference will now be made in detail to exemplary presently preferred embodiments, and for which FIG. 1A illustrates a generally sides (one side and one end) and top perspective view of an exemplary embodiment of a filter capacitor 20 in accordance with the presently disclosed technology, while FIGS. 1B and 1C respectively illustrate cross-sectional representations of the ground electrode 22 and signal electrode 24 internal geometry of the exemplary embodiment of present FIG. 1A. As understood by those of ordinary skill in the art from the complete disclosure herewith and accompanying illustrations, such electrodes 22 and 24 are received within dielectric material 26 forming the main body of filter capacitor 20. Such discrete vertical electrode filter arrangement mimics the electrical structure of a prior art discoidal feedthrough filter generally 28, as represented by subject FIG. 2.

Figure 1B:
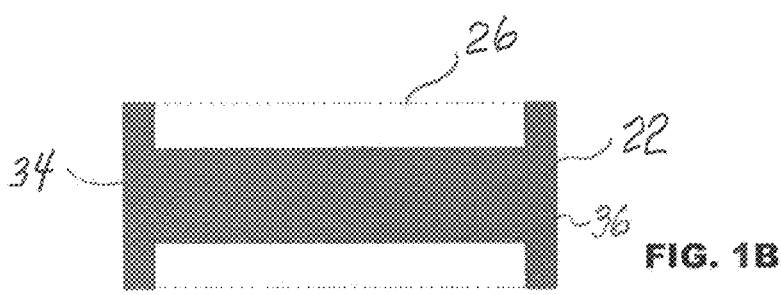
FIGS. 1B and 1C respectively illustrate cross-sectional representations of the ground electrode and signal electrode internal geometry of the exemplary embodiment of present FIG. 1A.
Figure 1C:
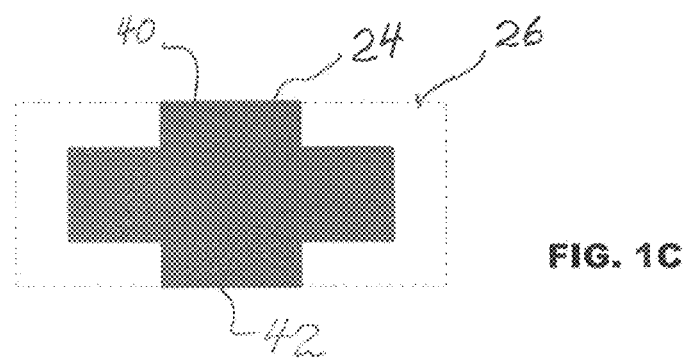
Figure 2:
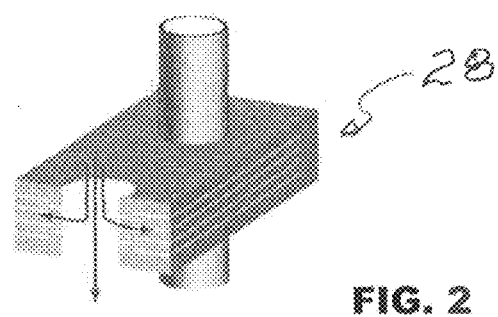
FIG. 2 represents electromagnetic flow lines of a prior art discoidal feedthrough filter, the electrical structure of which is mimicked by the presently disclosed exemplary embodiment of present FIG. 1A.

As shown by FIGS. 1B and 1C, the end terminations 30 and 32 of the FIG. 1A arrangement provide connection to ground electrode internal geometry ends 34 and 36, respectively, while the middle termination 38 provides connection to signal electrode internal geometry top projection 40. A bottom termination (not shown in FIG. 1A) provides connection to signal electrode internal geometry bottom projection 42.

The cross-sections of FIGS. 1B and 1C represent the vertical nature of the electrodes of the indicated exemplary embodiment relative to a supporting substrate or device or surface to which the embodiment will be mounted. Such discrete vertical electrode filter generally 20 is intended in one use thereof for mounting in relation to an AIMD (active implantable medical device).

Figure 3A:
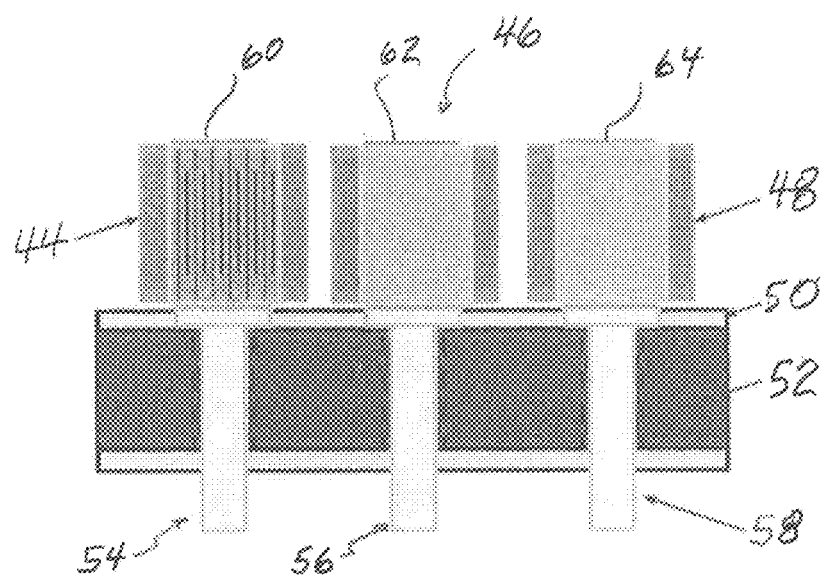
FIGS. 3A and 3B are respective side and top views illustrating conceptual layouts of filter conductors, positioned relative to a representative metal ferrule and insulating feedthrough.
Figure 3B:
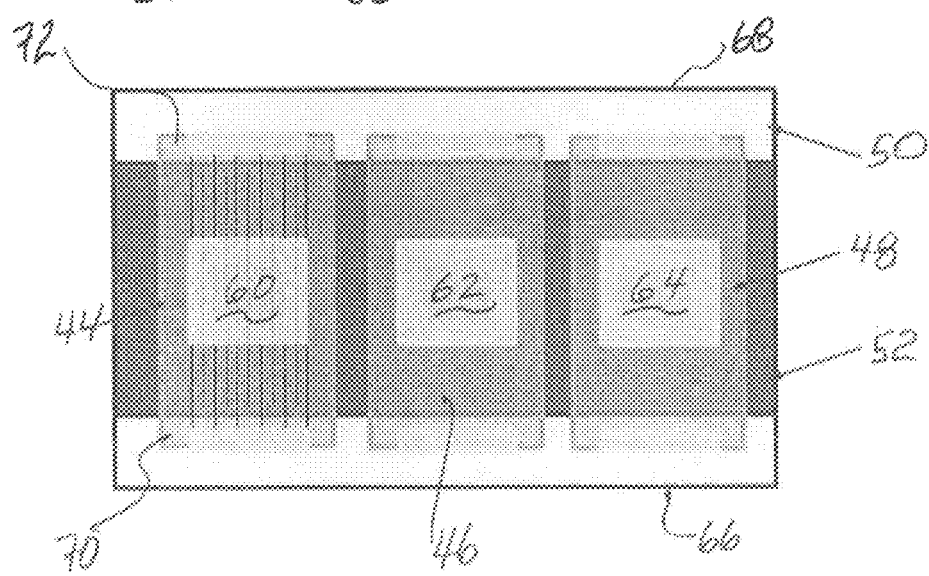

FIGS. 3A and 3B illustrate respective side and top views of conceptual layouts of filter conductors 44, 46, and 48, positioned relative to a representative metal ferrule 50 and insulating feedthrough 52. Also represented are wire conductors 54, 56, and 58 with which the discrete filters respectively associate.

As shown, such plurality of wire conductors 54, 56, and 58 (or pins in some instances) are supported through an insulating feedthrough 52, which is mounted relative to a metal ferrule 50. In practice, a corresponding plurality of the presently disclosed discrete vertical electrode filters 44, 46, and 48 (filter capacitors) mount to the metal ferrule for purposes of a ground connection and connect for input or signal purposes to the corresponding plurality of feedthrough conductors, as illustrated. Representative filter 44 is shown in partial see-through in both FIGS. 3A and 3B to illustrate the positioning of the vertical electrodes therein. As will be understood by those of ordinary skill in the art, the representative filter outputs (top side terminations) 60, 62, and 64 connect to internal circuitry of an associated implantable medical device (not shown) while the bottom side terminations thereof connect to their respective feedthrough conductors 54, 56, and 58. As shown, respective end terminations of the filter capacitors contact respective sides 66 and 68 of ferrule 50 for a ground connection. For example, respective end terminations 70 and 72 of filter capacitor 44 are electrically connected with members 66 and 68 of ferrule 50.

FIGS. 4A and 4B and FIGS. 5A through 5C illustrate various alternative features which may be used in conjunction with the presently disclosed subject matter for optimizing performance of particular embodiments, all as selected by those of ordinary skill in the art devising particular embodiments for particular needs or applications.

Figure 4A:
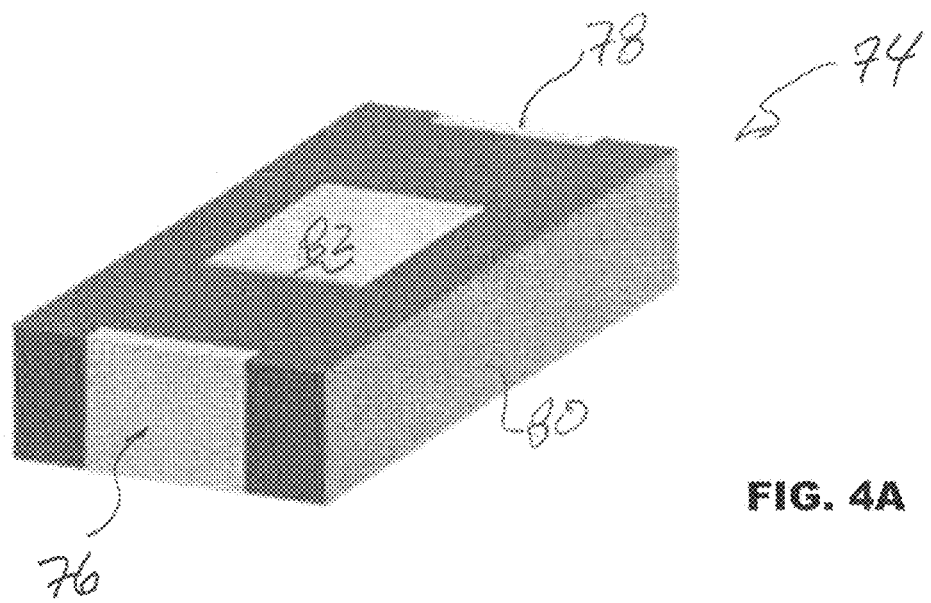
FIGS. 4A and 4B illustrate exemplary symmetric and asymmetric terminal arrangements as may be practiced with the presently disclosed subject matter.
Figure 4B:
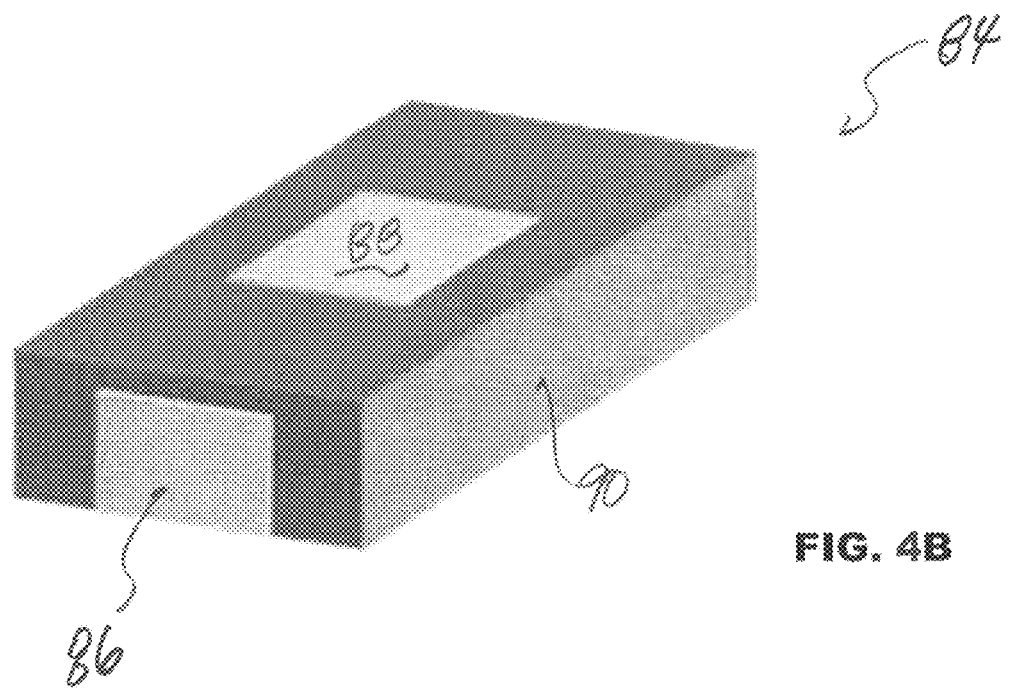

Low cost assembly features may be obtained in part with asymmetric dimensions (in comparison with symmetric terminals) as shown by the comparison between FIG. 4A (symmetric terminals) and FIG. 4B (asymmetric terminals). Representative filter 74 may have respective end terminations 76 and 78 on its dielectric body 80, which end terminations are symmetrically positioned on such body 80. Also, a top side termination 82 may be matched by a bottom side termination (not seen in FIG. 4A). Representative filter 84 may have only one end termination 86 to go along with its top side termination 88 (and a bottom side termination, not seen in FIG. 4B). As shown, such single end termination 86 is asymmetrical with reference to dielectric body 90 of filter 84. Such asymmetric arrangements may provide ease of orientation, and may provide for improved high voltage performance. Also, the use of plated terminals may permit reflow soldering techniques and conductive adhesives to be utilized. Further, the resulting structure (as represented by exemplary FIG. 4B) helps to keep ground features off the top surface, when so desired.

Figure 5A:
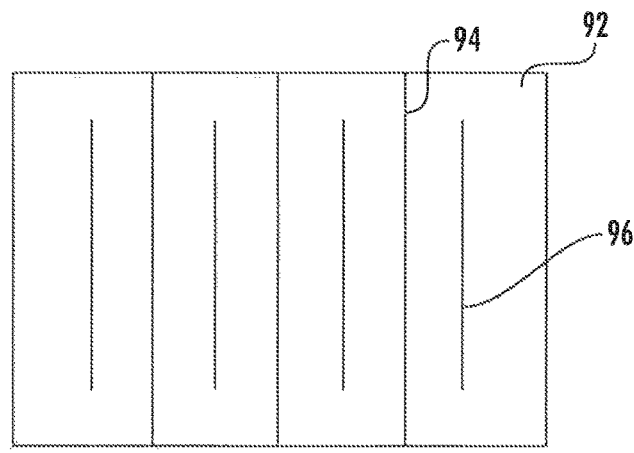
FIGS. 5A, 5B, and 5C illustrate respective approaches to lowering series resistance which may be practiced in conjunction with the presently disclosed subject matter, particularly representing standard design, Low dcR design and Low dcR/ESR design, respectively.
Figure 5B:
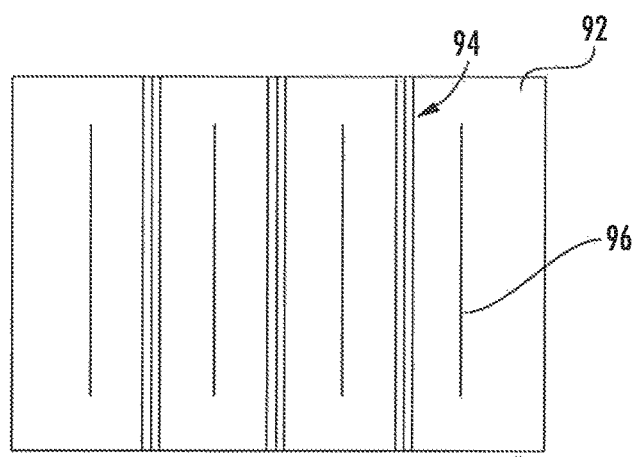
Figure 5C:
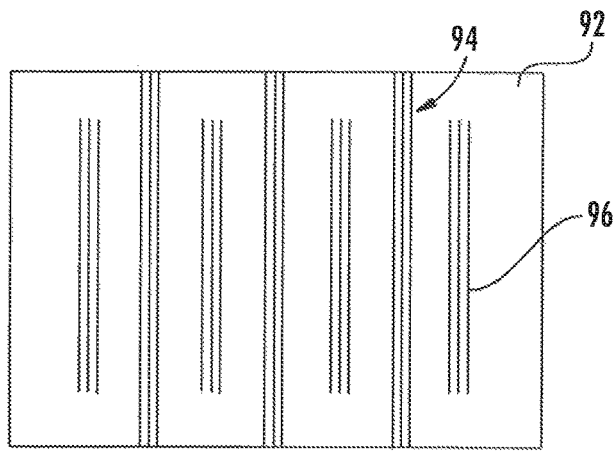

Relatively lower series resistance features may be accommodated by the presently disclosed subject matter, by incorporating a variety of approaches. As represented by FIGS. 5A, 5B, and 5C, such figures illustrate respective approaches to lowering series resistance which may be practiced in conjunction with the presently disclosed subject matter, particularly representing standard design, Low dcR design and Low dcR/ESR design, respectively. In essence, selected inner electrodes can be repeated to reduce dcR and ESR. Also, low resistance metals may be used such as nickel, copper, or high purity silver. As will be understood from the representative illustrations of such FIGS. 5A through 5C, a representative body of dielectric material 92 may have interleaved sets of electrodes 94 and 96. In FIG. 5B (representative relatively lower dcR design), electrodes 94 have been selectively repeated. In FIG. 5C, (representative relatively lower dcR and ESR design), both sets of electrodes 94 and 96 have been selectively repeated.

Further, presently disclosed subject matter may contribute to achieving relatively higher breakdown voltage, through incorporation for example of fine-grained dielectrics, and/or low-stress electrode geometries. Specialty configurations may also be accommodated, such as the use of low dielectric materials (for example, made from NPO dielectric materials) for RF connections, or involving short-circuited geometry to connect a ground pin to an outer shield.

Figure 6A:
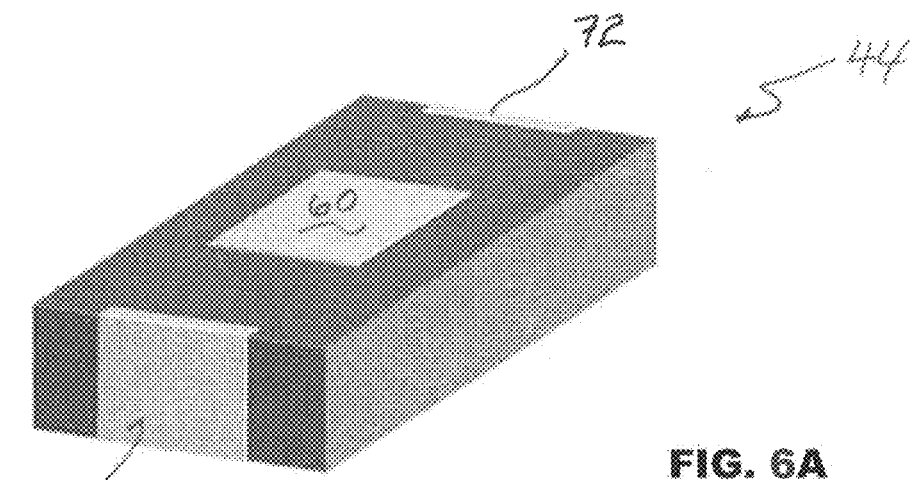
FIG. 6A is an exemplary embodiment of presently disclosed subject matter, similar to the illustrations of present application FIGS. 1A and 4A, and intended to be mounted on a ferrule and feedthrough as two of such embodiments (of FIG. 6A) are represented in mounted configuration by the perspective illustration of present FIG. 6B.
Figure 6B:
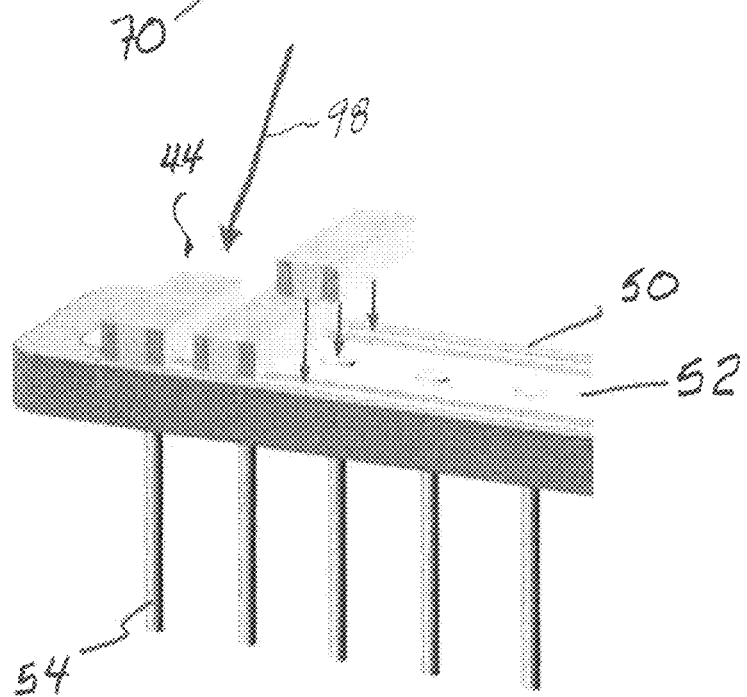

As represented by application FIGS. 6A and 6B, the presently disclosed methodology for mounting the subject discrete feedthrough filter on a ferrule/insulating feedthrough supporting surface uses surface tension of solder for self-alignment of the device during reflow. In other words, the surface tension causes auto-rotation and centering of the piece whenever the solder is heated up for reflow. Thereafter, a flex-circuit ribbon or nailhead lead (not shown) may be attached after mounting, to secure the arrangement.

FIG. 6A is an exemplary embodiment of presently disclosed subject matter, similar to the illustrations of present application FIGS. 1A, 3A, and 3B, and intended to be mounted on a ferrule and feedthrough as two of such embodiments (of FIG. 6A) are represented in mounted configuration by the perspective illustration of present FIG. 6B. The arrow 98 between FIGS. 6A and 6B show how an individual discrete device 44 according to the presently disclosed subject matter is mounted on an existing ferrule 50 and insulating feedthrough 52. In particular, the illustrated exemplary embodiment of FIG. 6A may have 0.126" L×0.050" W×0.060" H, a signal terminal ~0.030" sq, and a ground terminal 70 or 72 ~0.030" W having about 0.005" wrap. Further, such exemplary capacitor 44 embodiment may be built on CMAP with Ni electrodes and terminated with FCT (fine copper termination) plus NiSn or NiAu. Any thick-drop parts would require dummy electrode prints between active layers. Active layers can be doubled to reduce ESR.

Figure 7A:
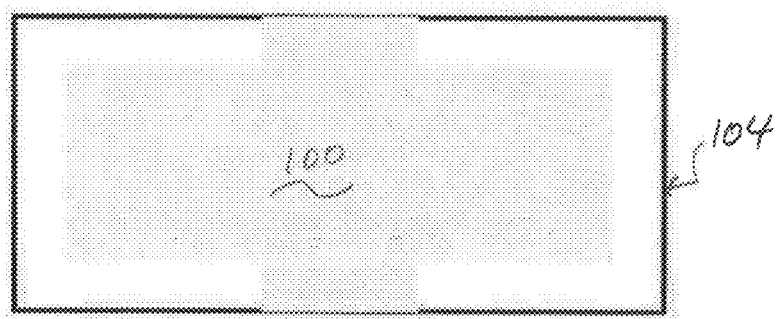
FIGS. 7A and 7B represent, respectively, side and end views of the signal layer internal structures of the exemplary embodiment of present FIG. 6A.
Figure 7B:
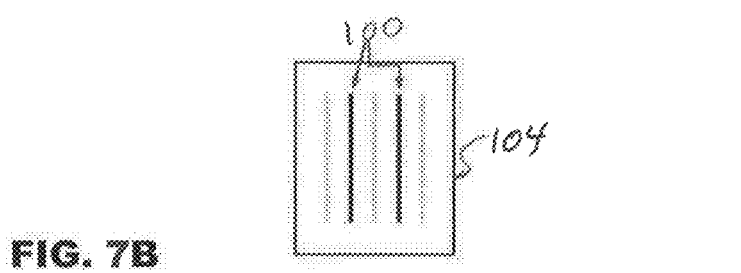
Figure 7C:
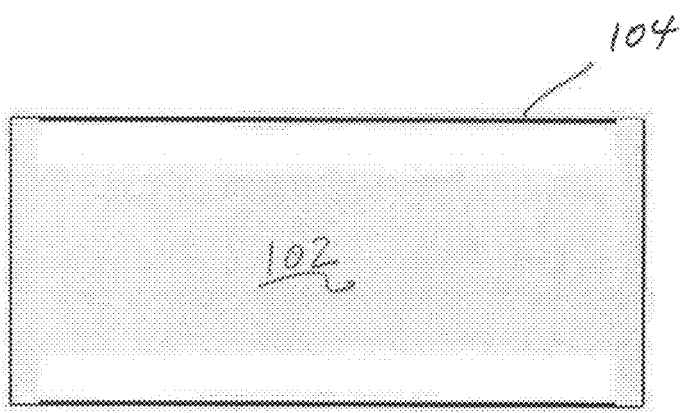
FIG. 7C represents the ground layer internal structures (side view) of the exemplary embodiment of present FIG. 6A.

FIGS. 7A and 7B represent, respectively, side and end views of the signal layer internal structures 100 for exemplary embodiment FIG. 6A, while FIG. 7C represents the ground layer internal structures 102 (side view) of such exemplary embodiment. The end view FIG. 7B shows how signal layers 100 may be alternately included within the dielectric 104 of the filter capacitor.

FIG. 7C representative ground layer 102 may be one of an exemplary embodiment which includes four active layers at 7.5 mil fired layer thickness. Per such embodiment, estimated capacitance using N370 dielectric is 1,500 pF. Thinner layers would allow part height (i.e., ESR) to be reduced.

Figure 7D:
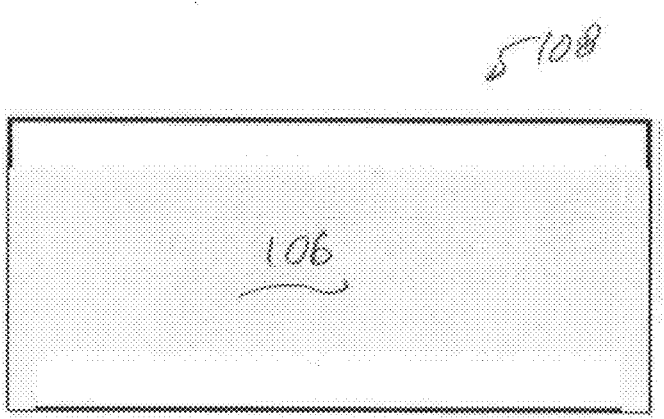
FIG. 7D illustrates an alternate ground pattern (alternative to FIG. 7C) which results with an asymmetric terminal (with no wrapping on the top surface)

FIG. 7D illustrates an alternative ground pattern 106 to that one shown by representative FIG. 7C. The result of such FIG. 7D alternative ground pattern is an asymmetric terminal configuration. As shown, that results in no wrapping of the termination on the top surface (generally 108) of the associated filter capacitor.

FIGS. 8A and 8B illustrate, respectively, end and top views (in partial see-through illustration) of a discrete vertical feedthrough filter (generally 110) of presently disclosed subject matter in combination with a supporting ferrule 112, insulating feedthrough 114, and terminal wire 116, similar to the perspective view combination of subject FIG. 6B. FIG. 8B illustrates the exemplary use of gold pads 118 on a Titanium ferrule element 112. FIG. 8C illustrates an enlarged top view in isolation of the presently disclosed discrete vertical feedthrough (FT) filter 110 otherwise shown in combination per the illustrations of subject FIGS. 8A and 8B. One example of an embodiment of such individual filter element 110 per presently disclosed subject matter would be a size 1305 chip with 30 mil wide Sn-plated terminations. FIG. 8B represents a plurality of such filters received on ferrule 112 and each respectively associated with its own terminal wire or feedthrough conductor 116. One such filter 110 is omitted from the illustration of FIG. 8B to better show the positioning of supporting pads 118 and one of the feedthrough conductors.

The two respective illustrations of subject FIG. 8D show top views of representative A and B patterns 120 and 122, respectively, for signal pins of the illustrated exemplary embodiment of present FIG. 8A. The illustration of subject FIG. 8E shows a top view of a representative pattern 124 for RF pins as may be associated with the illustrated exemplary embodiment of present FIG. 8A. In some instances, specialty configurations may also be accommodated, such as the use of low dielectric materials (made from NPO dielectric materials) for the representative RF connections. The illustration of subject FIG. 8F shows a top view of a representative pattern 126 for ground pins as may be associated with the illustrated exemplary embodiment of present FIG. 8A.

Beginning with a representative preliminary electrode layer design, present FIGS. 9A, 9B, and 9C, illustrate top views of respectively signal, ground, and dummy electrode layers 128, 130, and 132 of such design. As noted by the arrow lines 134 and 136 at the bottom of the FIG. 9A illustration and at the left middle side of the FIG. 9B illustration, respectively, the indicated elements are added features for a nucleate function occurring such as during an FCT (Fine Copper Termination, electroless plating) process. Alternatively, electrolytic plating or other plating may also be used in some embodiments. Similarly, the element 138 at the bottom of the FIG. 9C illustration represents a dummy electrode which may be used to nucleate the FCT process.

Subject FIGS. 10A, 10B, and 10C respectively illustrate signal, ground, and dummy electrode layers 140, 142, and 144 as presently disclosed for a shielded design for increasing DWV (dielectric withstand voltage). The shielding present in such layers will be understood by those of ordinary skill in the art from comparing the respective layer illustrations from FIGS. 9A through 9C to determine where there are added features (amounting to added shielding). For example, a comparison of the respective signal layers of FIGS. 9A and 10A shows additional protruding shielding members 146 from the top and bottom FCT nucleation members which otherwise appear at each vertical end of the signal layer 140. Similarly, comparison of the exemplary ground layers of respective FIGS. 9B and 10B represent enlarged (shielded) areas 148 around each end of the central top-to-bottom extending feature of the ground layer 142. Also, such a comparison between the dummy layers 144 represented by exemplary FIGS. 9C and 10C shows similar additional protruding shielding members 150 from the bottom and top FCT nucleation members 152 and 154, respectively in FIG. 10C relative to FIG. 9C, just as there were for FIG. 10A in comparison with FIG. 9A. Such added shielding features 150 result in increased dielectric withstand voltage (DWV) characteristics of the presently disclosed embodiments which incorporate such shielding features.

FIGS. 11A and 11B represent exemplary alternative device configurations which may be practiced in accordance with the presently disclosed subject matter. FIG. 11A makes use of a symmetrical terminal filter 74 similar to present FIG. 4A, while FIG. 11B makes use of an asymmetrical terminal filter 84 similar to present FIG. 4B. In particular, FIG. 11A represents a top view of a double-ended filter 74 as presently disclosed in association with a single row feedthrough 156 and associated ferrule 158. As shown, end terminations 76 and 78 are associated with respective lateral sides of ferrule 158. A top side termination 82 has a matching bottom side termination (not seen in FIG. 11A) which connects with its associated feedthrough conductor 160. FIG. 11B represents a top view of a single-ended filter 84 as presently disclosed in association with a double row feedthrough 164 and associated ferrule 166. The end terminal 86 of single-ended filter 84 is associated with one lateral side of ferrule 166, while a bottom side termination (not seen) opposite the top side termination 162 of filter 84 is associated with a respective one of feedthrough conductors 162. Another conductor 162' in the other line of double row feedthrough 164 is associated with a bottom side termination (not seen) of single-ended filter 84' which is opposite top side termination 88' thereof. As shown, the asymmetrical filters 84 and 84' may be used in alternately opposite positions, to respectively cover the respective rows of conductors of the dual row feedthrough 164. The positions of the conductors 162 and 162' illustrated with filters 84 and 84', respectively, are shown with dotted lines, since they otherwise in the top view of FIG. 11B are not visible below their respective filters.

Those of ordinary skill in the art will appreciate from the complete disclosure herewith various potential benefits from various presently disclosed embodiments. For example, in many instances, lower manufacturing costs may occur. Also, since discrete devices are contemplated, each device is not tied down to a specific associated component pitch. That makes the individual devices more universal in their potential applications. Additionally, with such improved universality of the feedthrough filters, that improves the ability for concurrent development of modifications of feedthrough structures for other facets or purposes of technology. Further, due to their discrete nature as associated with the various plurality of lead wires or pins (see, for example, FIGS. 3A, 6B, and 8B), there is substantial reduction in any cross-talk behavior between adjacent and/or nearby signal lines. Similarly, owing to their discrete nature, there is the opportunity for new development of interconnection schemes, for example, such as flex-circuit connections.

While the presently disclosed subject matter has been described in detail with respect to specific embodiments thereof, it will be appreciated that those skilled in the art, upon attaining an understanding of the foregoing may readily adapt the presently disclosed technology for alterations or additions to, variations of, and/or equivalents to such embodiments. Accordingly, the scope of the present disclosure is by way of example rather than by way of limitation, and the subject disclosure does not preclude inclusion of such modifications, variations, and/or additions to the presently disclosed subject matter as would be readily apparent to one of ordinary skill in the art.

What is claimed is:

1. A feedthrough filter arrangement for use with an AIMD, comprising:
   a ferrule;
   a feedthrough associated with said ferrule;
   a plurality of conductors supported through said feedthrough; and
   a corresponding plurality of discrete filters, each of said filters having at least two respective terminals, with one of said terminals associated with a respective one of said conductors, and the other of said terminals associated with said ferrule;

wherein
said at least two respective terminals comprise side and end terminals associated respectively with said filters and said ferrule; and
each of said filters has two sets of interleaved vertical electrodes comprising ground electrodes and signal electrodes wherein said ground electrodes are associated with at least one end terminal of each respective filter so that ground is connected to said ferrule, and wherein said signal electrodes are associated with at least one side terminal of each respective filler so that signals on a respective associated conductor are connected to such associated conductor.

2. A feedthrough filter arrangement as in claim 1, wherein said conductors comprise respective wire conductors for each of said discrete filters.

3. A feedthrough filter arrangement as in claim 1, wherein:
said ferrule comprises a metal ferrule; and
said feedthrough comprises an insulating cofired feedthrough which is mounted relative to said metal ferrule.

4. A feedthrough filter arrangement as in claim 1, wherein:
each of said filters has two sets of interleaved vertical electrodes comprising ground electrodes and signal electrodes;
each of said ground electrodes has respective projecting end portions connecting with respective end terminals of each of said filters; and
each of said signal electrodes has respective projecting side portions connecting with respective side terminals of each of said filters.

5. A feedthrough filter arrangement as in claim 1, wherein said respective side and end terminals comprise asymmetrical terminals.

6. A feedthrough filter arrangement as in claim 5, wherein said feedthrough includes a double row of conductors supported therethrough, and wherein said filters are mounted on said feedthrough in a row with end terminals thereof on alternate sides of said feedthrough.

7. A feedthrough filter arrangement as in claim 1, wherein the side terminals of said filters comprise respective top and bottom side terminals, with each bottom side terminal respectively connected to the associated conductor of its filter, and with each top side terminal connected to an associated AIMD.

8. A feedthrough filter arrangement as in claim 1, wherein said respective side and end terminals include at least a pair of end terminals for each respective filter, and comprise symmetrical terminals for each respective filter.

9. A feedthrough filter arrangement as in claim 8, wherein:
said ferrule comprises a titanium ferrule with sets of upper surface gold pads attached to ground of said ferrule; and
said filters are mounted relative to said ferrule such that said end terminals for each respective filter are attached to a set of said gold pads of said ferrule.

10. A feedthrough filter arrangement as in claim 8, wherein said conductors are supported in a single row in said feedthrough, and respective end terminals of each of said filters are mounted on opposite sides of said feedthrough, with a bottom side terminal of each of said elements situated over respective of said conductors.

11. A feedthrough filter arrangement as in claim 1, wherein at least some of said filters further include additional ground electrodes for relatively lower dcR filter characteristics.

12. A feedthrough filter arrangement as in claim 1, wherein at least some of said filters further include additional signal electrodes for relatively lower ESR filter characteristics.

13. A feedthrough filter arrangement as in claim 1, wherein at least some of said filters further include:
additional ground electrodes for relatively lower dcR filter characteristics; and
additional signal electrodes for relatively lower ESR filter characteristics; and
wherein said electrodes comprise relatively lower resistance metals.

14. A feedthrough filter arrangement as in claim 1, wherein said filters include relatively low dielectric materials made from NPO dielectric materials.

15. A feedthrough filter arrangement as in claim 1, wherein said filters further include a plurality of dummy electrode layers providing nucleation areas for plating formation of filter terminals.

16. A feedthrough filter arrangement as in claim 15, wherein said ground and signal electrodes and said dummy electrode layers include additional shielding members for relatively increasing the dielectric withstanding voltage characteristics of said filters.

17. A feedthrough filter arrangement for use in association with external circuitry, comprising:
a metal ferrule;
an insulating feedthrough associated with said ferrule;
a plurality of wire conductors supported through said feedthrough; and
a corresponding plurality of discrete cofired filter capacitors, each of said filter capacitors having:
respective end terminals;
a top side terminal;
a bottom side terminal;
a body of dielectric material; and
two sets of interleaved vertical electrodes comprising ground electrodes and signal electrodes received in said body of dielectric material, wherein each of said ground electrodes has respective projecting end portions connecting with respective end terminals of each of said filter capacitors, and each of said signal electrodes has respective projecting side portions connecting with respective side terminals of each of said filter capacitors;
wherein respective end terminals of each of said filter capacitors are mounted on opposite sides of said ferrule for a ground connection therewith, and with a bottom side terminal of each of said filter capacitors connected with a respective one of said conductors for a signal connection therewith, so that each of said top side terminals of said filter capacitors are exposed for respective connections with associated external circuitry.

18. A feedthrough filter arrangement as in claim 17, wherein at least some of said filter capacitors further include:
additional ground electrodes for relatively lower dcR filter capacitor characteristics; and
additional signal electrodes for relatively lower ESR filter capacitor characteristics.

19. A feedthrough filter arrangement as in claim 17, wherein:
said ferrule comprises a titanium ferrule with sets of upper surface gold pads attached to ground of said ferrule; and said filter capacitors are mounted relative to said ferrule such that said end terminals for each respective filter are attached to a set of said gold pads of said ferrule.

20. A feedthrough filter arrangement as in claim 17, wherein at least some of said filter capacitors further include a plurality of dummy electrode layers providing nucleation areas for plating formation of filter capacitor terminals.

21. A feedthrough filter arrangement as in claim 20, wherein said ground and signal electrodes and said dummy electrode layers include additional shielding members for relatively increasing the dielectric withstanding voltage characteristics of said filter capacitors.

22. Methodology for a feedthrough filter arrangement for use with an active implanted medical device (AIMD), comprising:
providing a metal ferrule;
fitting an insulating feedthrough with said ferrule;
supporting a plurality of conductors through said feedthrough, wherein the plurality of conductors are arranged in a double row; and
connecting respectively a corresponding plurality of discrete cofired filters with said plurality of conductors, so as to reduce cross-talk between signals on adjacent of said conductors, wherein each of said filters comprises at least one end terminal and at least one side terminal, and wherein said fitters are mounted on said feedthrough in a row with end terminals thereof on alternate sides of said feedthrough.

23. Methodology as in claim 22, wherein the at least one side terminal is associated with a respective one of said conductors, and the at least one end terminal is associated with said ferrule.

24. Methodology as in claim 23, further including providing said filter terminals as either symmetrical or asymmetrical terminals.

25. Methodology as in claim 23, wherein:
each of said filters has two sets of interleaved vertical electrodes comprising ground electrodes and signal electrodes, wherein said ground electrodes are associated with the at least one end terminal of each respective filter so that ground is connected to said ferrule, and wherein said signal electrodes are associated with the at least one side terminal of each respective filter so that signals on a respective associated conductor are connected to such associated conductor.

26. Methodology as in claim 25, wherein the at least one side terminal of said filters comprise respective top and bottom side terminals, with each bottom side terminal respectively connected to the associated conductor of its filter, and with each top side terminal connected to an associated AIMD.

27. Methodology as in claim 25, wherein each of said ground electrodes has respective projecting end portions connecting with respective end terminals of each of said filter capacitors, and each of said signal electrodes has respective projecting side portions connecting with respective side terminals of each of said filter capacitors.

28. Methodology as in claim 27, further including selectively providing additional electrodes to said filter capacitors for relatively lower dcR and/or relatively lower ESR filter characteristics.

29. Methodology as in claim 27, further including selectively providing a plurality of dummy electrode layers to said filter capacitors for providing nucleation areas for plating formation of filter capacitor terminals.

30. Methodology as in claim 29, further including selectively providing additional shielding members to selected of said ground and signal electrodes and said dummy electrode layers for relatively increasing the dielectric withstanding voltage characteristics of said filter capacitors.

31. Methodology as in claim 27, wherein said end terminals of said filter capacitors are mounted on said ferrule using surface tension of solder for self-alignment of said capacitors during a solder reflow step, which causes autorotation and centering of the capacitor whenever the solder is heated up for reflow.

32. Methodology as in claim 31, further including attaching a lead to said capacitor after said reflow step, to secure the positioning of said capacitor relative to said ferrule.

* * * * *